United States Patent [19]

Polywka et al.

[11] Patent Number: 5,801,248
[45] Date of Patent: Sep. 1, 1998

[54] STEREOSELECTIVE SYNTHESES

[75] Inventors: Mario Eugenio Cosamino Polywka, Didcot; Stephen Graham Davies, Oxford, both of Great Britain

[73] Assignee: Oxford Asymmetry International PLC., Abingdon, United Kingdom

[21] Appl. No.: 817,166

[22] PCT Filed: Oct. 20, 1995

[86] PCT No.: PCT/GB95/02484

§ 371 Date: Apr. 21, 1997

§ 102(e) Date: Apr. 21, 1997

[87] PCT Pub. No.: WO96/12726

PCT Pub. Date: May 2, 1996

[30] Foreign Application Priority Data

Oct. 20, 1994 [GB] United Kingdom .................. 9421208

[51] Int. Cl.⁶ .................................................. C07D 263/14

[52] U.S. Cl. .................................................. 548/228
[58] Field of Search .................................................. 548/228

[56] References Cited

PUBLICATIONS

Osman et al., *Journal of the Chemical Society of Japan*, vol. 48, No. 7, 1975, p. 2226.
Osman et al., *Chemical Abstracts*, vol. 85, No. 21, 22 Nov. 1976, abstract No. 160286f.
Alonso, *Chemical Abstracts*, vol. 123, No. 5, 31 Jul. 1995, abstract No. 56524z.
CA 123: 56524 Enantiospecific conversion . . . phenylalanine. Alonso et al., 1995.

*Primary Examiner*—Joseph McKane
*Attorney, Agent, or Firm*—Bacon & Thomas

[57] ABSTRACT

The present invention relates to the synthesis of chiral amino acids and to novel ferrocene-substituted oxazolidinone derivatives useful in such syntheses.

19 Claims, No Drawings

STEREOSELECTIVE SYNTHESES

This application is a 371 of PCT/GB95/02484 filed Oct. 20, 1995

This invention relates to the synthesis of chiral amino acids and to novel ferrocene-substituted oxazolidinone derivatives useful in such syntheses.

As is well known, the synthesis of chiral molecules in substantially enantiomerically pure form (which term is used herein to denote compounds containing at least 80%, advantageously at least 90%, and preferably at least 95% of a desired enantiomer) is of great importance, for example to the pharmaceutical industry, and much attention has been given to stereoselective syntheses which facilitate the preparation of such chiral compounds.

One area of interest within this general field is the stereoselective replacement of a hydrogen atom from the α-carbon atom of an α-amino acid (either natural or unnatural), e.g. by electrophilic substitution, to yield a chiral α-substituted α-amino acid. Products so obtained may, for example, be useful directly in the manufacture of pharmaceuticals or in preparing chiral auxiliaries of use in the synthesis of chiral molecules (see, for example, our International Patent Publication No. WO 95/18112). Existing methods for the preparation of such substituted α-amino acids either lead to products with insufficient enantiomeric purity, e.g. as a result of racemisation where the α-amino acid starting material is a substantially enantiomerically pure chiral compound, or give unacceptably low yields.

The present invention is based on our finding that highly efficient stereoselective substitution at the α-carbon atom of an α-amino acid may be effected if the α-amino acid or a carboxylate salt thereof is reacted with ferrocene carboxaldehyde or a derivative thereof to yield a Schiff's base which is then cyclised, e.g. by reaction with an acylating agent, to yield a chiral ferrocenyl-substituted 1,3-oxazolidin-5-one; the chirality of this molecule may derive from use of a chiral α-amino acid or, where glycine is chosen as the α-amino acid, from elsewhere in the molecule, e.g. by appropriate substitution of the ferrocene ring system or by use of a chiral acylating agent. We have found that such chiral oxazolidinones may be obtained in diastereomerically pure form and in substantially quantitative yield as the exclusively formed product; they may therefore be subjected to further reaction, e.g. to stereoselective electrophilic substitution at the α-carbon atom of the α-amino acid, without any intermediate separation step. Following such substitution the oxazolidinone may be cleaved to yield substantially enantiomerically pure α-substituted α-amino acid and to regenerate the ferrocene carboxaldehyde or derivative thereof.

Thus according to one aspect of the present invention there is provided use of ferrocene carboxaldehyde or a derivative thereof in the preparation of a substantially enantiomerically pure α-substituted α-amino acid, for example by stereoselective electrophilic substitution at the α-carbon atom thereof.

Viewed from another aspect the invention provides a process which comprises the steps:

(i) reacting an α-amino acid having at least one α-carbon-attached hydrogen atom or a carboxylate salt thereof (hereinafter referred to as the α-amino acid starting material) with ferrocene carboxaldehyde or a derivative thereof so as to yield a corresponding Schiff's base;

(ii) cyclising said Schiff's base to yield a chiral N-protected 2-ferrocenyl-substituted 1,3-oxazolidin-5-one (hereinafter referred to as the first chiral oxazolidinone);

(iii) subjecting said first chiral oxazolidinone to electrophilic substitution whereby said α-carbon-attached hydrogen atom is replaced by a substituent to yield a substantially enantiomerically pure second chiral oxazolidinone; and (iv) subjecting said second chiral oxazolidinone to ring cleavage so as to generate a substantially enantiomerically pure α-substituted α-amino acid (hereinafter referred to as the substituted α-amino acid product).

The above described process will now be described in greater detail with regard to the individual process steps, as follows:

Step (i)

The α-amino acid starting material may, for example, be a compound of general formula (I)

(where R represents a hydrogen atom or an organic group and X represents a hydrogen atom or a cation). It will be appreciated that when R is other than hydrogen the compound (I) will be chiral; it will normally be desirable to employ such starting materials in substantially enantiomerically pure form.

Where R represents an organic group this may, for example, be an aliphatic, cycloaliphatic or araliphatic group, e.g. containing up to 20 carbon atoms and optionally carrying one or more substituents. R may thus, for example, represent a group selected from $C_{1-10}$ alkyl (e.g. as in methyl, ethyl, propyl or butyl groups); $C_{2-10}$ alkenyl (e.g. vinyl or propenyl); $C_{3-10}$ cycloalkyl-$C_{1-4}$ alkyl (e.g. cyclopentylmethyl); $C_{6-12}$ carbocyclic aryl-$C_{1-4}$ alkyl (e.g. benzyl); heterocyclic aryl-$C_{1-4}$ alkyl (e.g. wherein the heterocyclic group comprises one or more 5- and/or 6-membered rings and contains at least one heteroatom selected from O, N and S); and substituted versions of any of the preceding groups, for example carrying one or more amino, carbamoyl, carboxyl, guanidino, hydroxyl, alkoxy (e.g. methoxy), mercapto or methylthio groups, protected as necessary.

Where X represents a cation this may be inorganic or organic. Representative inorganic cations include those derived from alkali and alkaline earth metals, for example sodium or potassium. Representative organic cations include those derived from strongly basic amines, for examples tertiary amines such as trialkylamines.

One useful class of starting materials (I) comprises compounds in which R is the α-substituent of a natural α-amino acid or an enantiomer thereof. Preferred R groups thus include methyl, isopropyl, isobutyl, sec-butyl, hydroxymethyl, 1-hydroxyethyl, mercaptomethyl, carboxymethyl, 2-carboxyethyl, carbamoylmethyl, 2-carbamoylethyl, 2-(methylthio)ethyl, 4-aminobutyl, benzyl, p-hydroxybenzyl, indol-3-ylmethyl, imidazol-4-ylmethyl or 3-guanidinopropyl. It will be appreciated that it may be necessary to protect reactive substituents such as amino, carboxyl, hydroxyl or thiol groups in such R groups, for example using appropriate blocking groups, e.g. such as are known in the art, during the course of processing of compounds (I) in accordance with the invention.

Derivatives of ferrocene carboxaldehyde which may be used in accordance with the invention carry one or more further ring substituents in addition to the carboxaldehyde group. The ferrocene carboxaldehyde or derivative thereof may therefore, for example, be a compound of general formula (II)

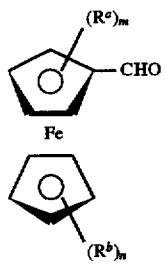

(II)

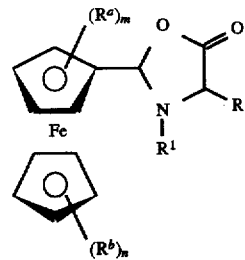

(IV)

(where m is 0 or an integer of 1–4, n is 0 or an integer of 1–5, and $R^a$ and $R^b$ represent substituting atoms or groups). It will be appreciated that where the compound (II) contains more than one of $R^a$ and/or $R^b$ these may represent different atoms or groups.

$R^a$ and $R^b$ may, for example, be selected from lower (e.g. $C_{1-6}$) alkyl (e.g. methyl, ethyl, propyl or butyl groups, such as t-butyl), lower alkoxy (e.g. methoxy or ethoxy), lower alkylthio (e.g. methylthio), lower alkylsulphonyl (e.g. methylsulphonyl), lower alkanoyl (e.g. acetyl), lower alkanoyloxy (e.g. acetoxy), lower alkoxycarbonyl (e.g. methoxycarbonyl), disubstituted amino (e.g. di(lower alkyl) amino such as dimethylamino), disubstituted aminoalkyl (e.g. di(lower alkyl)amino lower alkyl such as dimethylaminomethyl or 1-dimethylaminoethyl), lower alkanoylamino (e.g. acetamido), $C_{6-12}$ aryl-$C_{1-4}$ alkyl (e.g. benzyl or phenethyl), $C_{6-20}$ aryl (e.g. phenyl or naphthyl), carbamoyl, sulphamoyl, nitro and halo (e.g. chloro, bromo or iodo).

One of $R^b$ may advantageously be a carboxaldehyde group, thereby permitting one mole of the ferrocene carboxaldehyde derivative to react with two moles of the α-amino acid starting material.

The α-amino acid starting material and ferrocene carboxaldehyde or derivative thereof may be reacted under any appropriate conditions, for example at ambient temperature in an appropriate mutual solvent, for example an alcohol such as ethanol. Stoichiometric amounts of the two reagents are preferably employed.

Where starting materials of formulae (I) and (II) are employed, the Schiff's base product from this reaction step may be represented by general formula (III)

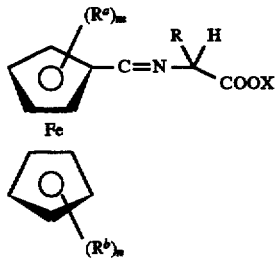

(III)

(where R, $R^a$, $R^b$, X, m and n are as hereinbefore defined). Such compounds are novel and constitute a feature of the present invention. It will be appreciated that, where one of $R^b$ in general formula (II) represents a carboxaldehyde group this will become a group —C=N—CH(R)—COOX in general formula (III).

Step (ii)

Cyclisation of the Schiff's base may conveniently be effected by reaction with a compound serving to introduce an N-protecting group at the imine nitrogen atom, e.g. to yield a compound of general formula (IV)

(where R, $R^a$, $R^b$, m and n are as hereinbefore defined and $R^1$ represents an N-protecting group) in the case of cyclisation of a compound of general formula (III). Such compounds are novel and constitute a feature of the present invention. It will be appreciated that when one of $R^b$ in general formula (III) represents a group —C=N—CH(R)—COOX this will become an oxazolidinone group in general formula (IV).

An important advantage of the invention is the diastereomeric purity of products such as compounds of general formula (IV) formed in this reaction step.

Representative N-protecting groups which may be used in the cyclisation step include lower alkanoyl such as acetyl, haloacetyl (e.g. trichloroacetyl), propionyl, isobutyryl or pivaloyl, e.g. introduced by reaction with an appropriate acylating agent, for example an acid anhydride or an acyl halide such as the chloride; lower alkoxycarbonyl such as t-butoxycarbonyl or 2,2,2-trichloroethoxycarbonyl, e.g. introduced by reaction with an appropriate haloformate such as the chloroformate; sulphonyl, including lower alkyl sulphonyl such as trifluoromethanesulphonyl and aryl sulphonyl such as p-toluenesulphonyl, e.g. introduced by reaction with an appropriate sulphonyl halide such as the chloride; and silyl, for example tri(lower alkyl) silyl such as trimethylsilyl, triisopropylsilyl or t-butyldimethylsilyl, e.g. introduced by reaction with an appropriate silyl halide such as the chloride. As described hereinafter it may be desirable to introduce a chiral N-protecting group such as camphanyl or camphasulphonyl, e.g. by reaction with the corresponding chlorides.

$R^1$ may if desired be derived from the C-terminal of a polypeptide whereby a new polypeptide may be obtained by hydrolysis of the compound (IV).

The cyclisation reaction may be carried out under any appropriate conditions, for example at ambient or reduced temperature in an appropriate mutual solvent, for example a halogenated hydrocarbon such as dichloromethane in the case of reaction with an acylating agent such as an acyl halide. Stoichiometric amounts of the two reagents are preferably employed.

Step (iii)

Compounds of general formula (IV) where R is other than hydrogen possess chirality at the 4-position of the oxazolidinone ring and will undergo stereospecific electrophilic substitution at this position to yield a substantially enantiomerically pure second chiral oxazolidinone.

Compounds of general formula (IV) where R is hydrogen, i.e. where the α-amino acid starting material is glycine or a carboxylate salt thereof, do not possess chirality at this position, and in such cases it will be necessary for there to be chirality elsewhere in the molecule so as to control the direction of electrophilic substitution at the 4-position of the oxazolidinone ring and ensure formation of a substantially enantiomerically pure second chiral oxazolidinone. Thus, for example, an asymmetric pattern of substituents $R^a$ may be present, preferably in the form of a single substituent ortho to the carboxaldehyde group in general formula (II). Where in this embodiment one of $R^b$ in general formula (II) represents a carboxaldehyde group a similar single ortho substituent is preferably present, its position being such that the meso configuration is avoided. It may be advantageous in such cases for the ortho substituent to be relatively bulky and/or chelating in order to enhance its directing effect. Alternatively, as noted above, chirality may be imparted to a compound (IV) in which R is hydrogen by the presence of a chiral $R^1$ group.

Sources of electrophiles which may be used in this reaction step include, for example, aliphatic and araliphatic halides, epoxides, aldehydes and ketones. The oxazolidinone starting material is preferably reacted with a strong base capable of promoting enolisation of the 5-keto group (e.g. a Group IA, IIA or IIIA metal alkyl, metal alkyl halide, metal alkyl trifluoroacetate or metal alkylamine such as lithium diisopropylamide), either during or, more preferably, before reaction with the source of electrophile. The reactions with the base and electrophile are preferably carried out in an inert solvent, e.g. a cyclic ether such as tetrahydrofuran, at a temperature of 0° C. or less, e.g. −78° C., if desired under an inert atmosphere, e.g. of nitrogen.

In the case of reaction of a compound of general formula (IV) the electrophilically substituted product may be represented by general formula (V)

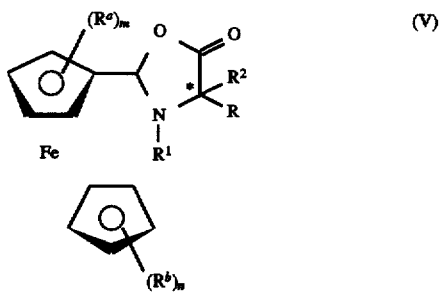

(where R, $R^1$, $R^a$, $R^b$, m and n are as hereinbefore defined, $R^2$ represents an organic group which is the residue of an electrophile, and the asterisk denotes that the configuration of R and $R^2$ is such that the compound is in substantially enantiomerically pure form). Such compounds are novel and constitute a feature of the present invention. It will be appreciated that where one of $R^b$ in general formula (IV) represents an oxazolidinone group this will become a corresponding substituted oxazolidinone group in general formula (V).

Representative $R^2$ groups in the above general formula (V) include aliphatic and araliphatic groups, e.g. containing up to 20 carbon atoms and optionally carrying one or more substituents. $R^2$ may thus, for example, represent a group selected from optionally substituted $C_{1-10}$ alkyl (e.g. as in methyl, cyanomethyl, ethyl, propyl or butyl groups); optionally substituted $C_{2-10}$ alkenyl (e.g. allyl or crotyl); optionally substituted $C_{6-12}$ carbocyclic aryl-$C_{1-4}$ alkyl (e.g. benzyl, 2-methylbenzyl or naphthylmethyl such as naphth-2-ylmethyl); optionally substituted heterocyclic aryl-$C_{1-4}$ alkyl (e.g. wherein the heterocyclic group comprises one or more 5- and/or 6-membered rings and contains at least one heteroatom selected from O, N, and S, for example as in N-protected indolylmethyl such as 1-t-butoxycarbonylindol-3-ylmethyl); and optionally substituted $C_{6-12}$ carbocyclic aryl-$C_{2-4}$ alkenyl and heterocyclic aryl-$C_{2-4}$ alkenyl groups (e.g. cinnamyl).

Step (iv)

Ring cleavage of the second chiral oxazolidinone may conveniently be effected by acid or base catalysed hydrolysis, e.g. using an acidic or basic ion exchange catalyst resin or an inorganic acid or base, for example an alkali metal hydroxide such as lithium hydroxide. Such hydrolytic cleavage may conveniently be carried out in an aqueous/organic solvent system such as aqueous acetone.

It will be appreciated that the reaction conditions for the ring cleavage and the nature of the N-protecting group at the 3-position of the oxazolidinone ring may advantageously be chosen so that ring cleavage is accompanied by N-deprotection, e.g. leading to formation of a substituted α-amino acid product of general formula (VI)

(where R, $R^2$, X and the meaning of the asterisk are as hereinbefore defined) or an acid addition salt thereof in the case of cleavage of a compound of general formula (V).

The reaction conditions are preferably also such that the ferrocene carboxaldehyde or derivative thereof is regenerated.

The following non-limitative examples serve to illustrate the invention.

EXPERIMENTAL TECHNIQUES

Melting points (m.p.) were obtained using a Thermogalen™ III melting point apparatus and are uncorrected.

Optical rotations were measured with a Perkin-Elmer 241 polarimeter with a thermally jacketted 10 cm cell at approximately 20° C. and are given in units of $10^{-1}$ deg $cm^2$ $g^{-1}$. Concentrations (c) are given in g/100 ml.

Infrared (IR) spectra were recorded as thin films between sodium chloride plates, as potassium bromide discs or in chloroform solution on a Perkin-Elmer 1750 Fourier Transform spectrometer. Absorptions are reported in wavenumbers ($cm^{-1}$). The following abbreviations are used: w, weak; m, medium; s, strong and br, broad.

Proton magnetic resonance spectra ($^1H$ NMR) were recorded at 200 MHz on a Varian Gemini 200 or Bruker AC200 spectrometer, at 300 MHZ on a Bruker WH300 and at 500 MHz on a Bruker AM500 spectrometer. For $^1H$ NMR recorded in $CDCl_3$, $CH_3OD$ and $D_2O$, chemical shifts ($\delta_H$) are quoted in parts per million (p.p.m.) and are referenced to the residual solvent peak. The following abbreviations are used: s, singlet; d, doublet; t, triplet; q, quartet; m, multiplet and br, broad. Coupling constants (J) were recorded in Hertz to the nearest 0.5 Hz.

Carbon magnetic resonance spectra ($^{13}C$ NMR) were recorded at 50.31 MHz on a Varian Gemini 200 or Bruker AC200 spectrometer and at 125.77 MHz on a Bruker AMX500 spectrometer using DEPT editing. Chemical shifts ($\delta_c$) are quoted in p.p.m. and referenced to $CDCl_3$ and $CH_3OD$ unless otherwise stated. Spectra recorded in $D_2O$ are referenced to internal 1,4-dioxane.

Diastereomeric excesses (d.e.) were determined by peak integration of the crude reaction products' $^1H$ and $^{13}C$ NMR spectra. Enantiomeric excesses (e.e.) were obtained using (R)-(−)- or (S)-(+)-1-(9-anthryl)-2,2,2-trifluoroethanol as a chiral shift reagent on crude reaction samples.

Low resolution mass spectra (m/z) were recorded on a VG Micromass ZAB 1F (CI/DCI/FAB), a VG Masslab 20-250 (CI/DCI) or a VG BIO Q (electrospray) spectrometer, with only molecular ions ($M^+$), fragments from molecular ions and major peaks being reported.

Column chromatography was performed on silicagel (Kiesel 60) or Amberlyst-15 resin. TLC was carried out with precoated silicagel 60 F-254 plates.

Anhydrous dichloromethane was obtained by distillation from calcium hydride under nitrogen. Anhydrous diethyl ether and anhydrous tetrahydrofuran were obtained by distillation from sodium/benzophenone ketyl under nitrogen. Petroleum refers to light petroleum (b.p. 40°–60° C.), redistilled before use. Ferrocenecarboxaldehyde and D,L-α-methylphenylalanine were purchased from Aldrich, the former being purified by flash chromatography (silicagel-diethyl ether) before use. Pivaloyl chloride was purified by bubbling nitrogen into the liquid and by distillation from calcium chloride and alumina (under nitrogen).

All reactions were performed under an atmosphere of dry nitrogen.

EXAMPLE 1

Ferrocenecarboxaldehyde sodium L-alaninate imine

Aqueous sodium hydroxide (11.2 mmol in 11 ml of water) was added to L-alanine (1.0 g, 11.22 mmol) and stirred for several minutes at room temperature. The solvent was removed in vacuo and the residue dried at 60° C. under high vacuum overnight. 4 Å molecular sieves, ferrocenecarboxaldehyde (11.78 mmol, 2.52 g) and absolute ethanol (50 ml) were added to the alaninate and stirred for 5 hours; the course of the reaction can be followed by IR. The molecular sieves were separated by filtration, the filtrate concentrated on a vacuum line and a red solid was obtained. Pentane (50 ml) was added and the mixture was stirred until a suspension was formed. This was filtered through a sinter and the residue was washed with pentane and dried under vacuum to give the title compound as a yellow-orange solid (3.28 g, 950%); $v_{max}$ (KBr disc) 1641 s (C=N) and 1591 ($CO_2^-$) $cm^{-1}$. The imine rapidly undergoes hydrolysis on silica or in the presence of water.

EXAMPLE 2

(2S,4S)-2-Ferrocenyl-4-methyl-3-pivaloyl-1,3-oxazolidin-5-one

4 Å Molecular sieves and dichloromethane (90 ml) were added to the product from Example 1 (3 g, 9.77 mmol), the mixture was cooled to −18° C., then recently distilled pivaloyl chloride (1.21 ml, 9.77 mmol) dissolved in dichloromethane (10 ml) was added dropwise. The resulting mixture was stirred overnight while being allowed to warm up to room temperature. The reaction mixture was filtered, and the filtrate was concentrated on a vacuum line (in the absence of heat to avoid racemisation taking place). Several portions of diethyl ether were added and then quickly passed through a sinter containing silica and celite. The ether was removed on a vacuum line without heating to give the title compound (3.42 g, 95%) as yellow crystals with >98% d.e. (>98% e.e. for the major diastereoisomer); m.p. 105° C.; $R_f$ 0.38 (petroleum-diethyl ether; 7:3); $[\alpha]_D^{25}$+21.5 (c 1.0, $CHCl_3$); $v_{max}$ (KBr disc) 3097 (HC=C), 1796 (OC=O) and 1643 (NC=O)$cm^{-1}$; $\delta_H$ (200 MHz; $C_6D_6$) 0.90 (9H, s, C(C$\underline{H}_3$)$_3$), 1.26 (3H, d, J 7 Hz, CHC$\underline{H}_3$), 3.86–3.91 (2H, m, Cp), 4.07 (5H, s, Cp'), 4.11–4.12 (1H, m, Cp), 4.23 (1H, q, J 7 Hz, C$\underline{H}$CH$_3$), 4.70–4.71 (1H, m, Cp) and 7.10 (1H, S, OC$\underline{H}$N); $\delta_H$ (200 MHz, $CDCl_3$) 1.27 (9H, s, C(C$\underline{H}_3$)$_3$), 1.56 (3H, d, J 7 Hz, CHC$\underline{H}_3$), 4.18–4.23 (3H, m, Cp), 4.25 (5H, s, Cp'), 4.59–4.61 (1H, m, Cp), 4.64 (1H, q, J 7 Hz, C$\underline{H}$CH$_3$) and 7.07 (1H, s, OC$\underline{H}$); $\delta_C$ (50.3 MHz; $CDCl_3$) 20.0 (CH$\underline{C}$H$_3$), 28.1 (C($\underline{C}$H$_3$)$_3$), 39.9 ($\underline{C}_3$)$_3$), 52.0 ($\underline{C}$HCH$_3$), 65.3, 67.8, 68.4, 69.2, 85.0 (9×$\underline{C}$H in Cp and Cp'), 88.7 (O$\underline{C}$HN), 173.5 and 175.8 (2×$\underline{C}$=O); m/z 370 [(M+H)$^+$, 100%], 369 [(M$^+$), 28], 240[39], 215[13] and 156[11]; (Found: C, 61.98; H, 6.57; N, 3.77; $C_{19}H_{23}NO_3Fe$ requires C, 61.80; H, 6.28; N, 3.79%). No starting ferrocenecarboxaldehyde was detected; were any to be present it may be removed by washing with cold pentane.

General Procedure to Form (2S,4R)-4-substituted-2-ferrocenyl-4-methyl-3-pivaloyl-1,3-oxazolidin-5-ones 1.6M n-Butyllithium (1 eq) was added dropwise to a solution in tetrahydrofuran at 0° C. of diisopropylamine (1.1 eq) recently distilled from calcium hydride, and the mixture was stirred for 15 minutes. The resulting solution was cooled to −78° C. and then transferred via cannula to a precooled (−78° C.) solution of the oxazolidinone from Example 2 (1 eq) in tetrahydrofuran. Then the appropriate electrophile (1.3 eq) was added dropwise and the reaction mixture was stirred overnight while being allowed to warm up to room temperature. The reaction mixture was concentrated on a vacuum line. Several portions of diethyl ether were added and then quickly passed through a sinter containing silica and celite. The ether was removed on a vacuum line to yield title compound and the d.e. and e.e. of the major diastereomer were determined. The product was then washed with cold pentane.

EXAMPLE 3

(2S,4R)-4-Benzyl-2-ferrocenyl-4-methyl-3-pivaloyl-1,3-oxazolidin-5-one

Starting with 3.0 g of the oxazolidinone from Example 2 and following the above general procedure using benzyl bromide as electrophile, the title compound (3.36 g, 90%) was obtained as yellow crystals with >98% d.e. (>98% e.e. for the main diastereomer); m.p. 159°–160° C.; $R_f$ 0.34 (petroleum-diethyl ether; 8:2); $[\alpha]_D^{25}$−191.5 (c 1.0, $CHCl_3$). After one crystallization the product showed $[\alpha]_D^{25}$−195.0 (c, 1.0, $CHCl_3$); $V_{max}$ (KBr disc) 3107 (HC=C), 1790 (OC=O) and 1629 (NC=O)$cm^{-1}$; $\delta^H$ (300 MHz; $CDCl_3$) 0.81 (9H, s, C(C$\underline{H}_3$)$_3$), 2.04 (3H, s, NCC$\underline{H}_3$), 3.21 (1H, d, J 13.5 Hz, C$\underline{H}_A$H$_B$), 3.81 (1H, d, J 13.5 Hz, CH$_A$$\underline{H}_B$), 4.21 and 4.25–4.26 (4H, 2 m, Cp), 4.28 (5H, s, Cp'), 6.10 (1H, s, OC$\underline{H}$N), 7.12–7.15 and 7.24–7.28 (5H, 2 m, $C_6\underline{H}_5$); $\delta_C$ (50.3 MHz; $CDCl_3$) 23.6 (NC$\underline{C}$H$_3$), 28.1 (C($\underline{C}$H$_3$)$_3$), 40.8 ($\underline{C}$(CH$_3$)$_3$), 41.3 ($\underline{C}$H$_2$), 66.2, 67.9, 68.6, 68.7, 69.1, 69.3 (9× $\underline{C}$H in Cp and Cp'), 86.7 (O$\underline{C}$HN), 89.1 (N$\underline{C}$CH$_3$), 176.1 and 176.6 (2×$\underline{C}$=O); m/z 460 [(M+H)$^+$, 100%)], 459 [(M$^+$), 33], 331[21], 330[50] and 199[27]; (Found: C, 67.79; H, 6.26; N, 3.28; $C_{26}H_{29}NO_3Fe$ requires C, 67.98; H, 6.36; N, 3.05%).

EXAMPLE 4

(2S,4R)-4-Allyl-2-ferrocenyl-4-methyl-3-pivaloyl-1,3-oxazolidin-5-one

Starting with 2.135 g of the oxazolidinone from Example 2 and following the above general procedure using distilled allyl bromide as electrophile, the title compound was obtained as orange crystals (1.843 g, 78%) with >95% d.e. (>96% e.e. for the major diastereomer); $R_f$ 0.82 (petroleum-diethyl ether; 5:5); m.p. 167°–169° C.; $[\alpha]^{25}_D$−218.2 (c 1.0, $CHCl_3$);$v_{max}$ (KBr disc) 3090 m (C—H), 1795 s (OC=O), 1651 s (NC=O), 1353 s and 1186 s $cm^{-1}$; $\delta_H$ (300 MHz; $CDCl_3$) 1.05 (9H, s, C(C$\underline{H}_3$)$_3$), 1.92 (3H, s, NCC$\underline{H}_3$), 2.53 (1H, dd, J 4 Hz, 9.5 Hz, C$\underline{H}_A$H$_B$—CH), 3.36 (1H, dd, J 6 Hz, 9.5 Hz, CH$_A$$\underline{H}_B$—CH), 4.20–4.24 and 4.28–4.32 (4H, 2 m, Cp), 4.23 (5H, s, Cp'), 5.10 (1H, s, CH=CH$_A$H$_B$), 5.15 (1H, d, J 2.5 Hz, CH=CH$_A$H$_B$), 5.47–5.61 (1H, m, CH$_2$—CH=CH$_2$ and 6.66 (1H, s, OCHN); $\delta_c$ (50.3 MHz; CDCl$_3$) 22.87 (NCCH$_3$), 28.68 (C(CH$_3$)$_3$), 39.57 (CH$_2$CH=CH$_2$), 41.09 (C(CH$_3$)$_3$), 64.71 (NCCH$_3$), 67.41, 68.08, 69.05 and 69.20 (9×CH in Cp and Cp'), 86.51 (OCHN), 89.77 (quaternary C in Cp), 120.04 (CH$_2$—CH=CH$_2$), 131.62 (CH$_2$—CH=CH$_2$), 175.47 and 175.99 (2×C=O); m/z (electron ionisation) 410 [ (M+H)$^+$, 13%], 409 [(M)$^+$, 73], 121 [57] and 57 [(C$_4$H$_9$)$^+$, 100]; (Found C 64.53, H 6.87, N 3.36; C$_{22}$H$_{27}$NO$_3$Fe requires C 64.56, H 6.65, N 3.42%).

EXAMPLE 5

(2S,4R)-4-Crotyl-2-ferrocenyl-4-methyl-3-pivaloyl-1,3-oxazolidin-5-one

Starting with 226.8 mg of the oxazolidinone from Example 2 and following the above general procedure using distilled crotyl bromide as electrophile, the title compound was obtained; $\delta_H$ (200 MHZ; CDCl$_3$) 1.06 (9H, s, C(CH$_3$)$_3$), 1.64 (3H, d, J 6.5 Hz, CH=CHCH$_3$), 1.89 (3H, s, NCCH$_3$), 2.45 (1H, dd, J 6 Hz, 13.5 Hz, CH$_A$H$_B$), 3.28 (1H dd, J 10 Hz,13.5 Hz, CH$_A$H$_B$), 4.18–4.36 (4H, m, Cp), 4.27 (5H, s, Cp'), 5.06–5.24 (1H, m, CH$_2$CH=CHCH$_3$), 5.52 (1H, dd, J 6.5 Hz, 15.5 Hz, CH$_2$CH=CHCH$_3$) and 6.64 (1H, s, OCHN).

EXAMPLE 6

(2S,4R)-4-(2-Methylbenzyl)-2-ferrocenyl-4-methyl-3-pivaloyl-1,3-oxazolidin-5-one Starting with 2.088 g of the oxazolidinone from Example 2 and following the above general procedure using α-bromo-o-xylene as electrophile, the title compound was obtained as yellow crystals (2.379 g, 89%) with >96% d.e. (>84% e.e. for the major diastereomer); m.p. 155°–157° C.; [α]$^{23}_D$ –180.1 (c 1.1, CHCl$_3$); ν$_{max}$ (KBr disc) 2970 m (C—H), 1790 s (OC=O), 1627 s (NC=O), 1336 s and 1177 s cm$^{-1}$; $\delta_H$ (200 MHz; CDCl$_3$) 0.72 (9H, s, (CH$_3$)$_3$), 2.08 (3H, s, NCCH$_3$), 2.36 (3H, s, C$_6$H$_4$CH$_3$), 3.28 (1H, d, J 14.5 Hz, CH$_A$H$_B$), 3.82 (1H, d, J 14.5 Hz, CH$_A$H$_B$), 4.21–4.32 (4H, m, Cp), 4.29 (5H, s, Cp'), 6.33 (1H, s, OCHN) and 7.02–7.13 (4H, m, C$_6$H$_4$CH$_3$); $\delta_c$ (50.3 MHz; CDCl$_3$) 19.63 and 24.28 (2×CH$_3$), 27.86 (C(CH$_3$)$_3$), 37.55 (CH$_2$), 40.85 ( C(CH$_3$)$_3$), 65.16 (NCCH$_3$), 67.78, 68.79, 68.94 and 69.31 (9×CH in Cp and Cp'), 86.93 (OCHN), 89.58 (quaternary C in Cp), 125.88, 126.93, 128.53 and 131.22 (4×CH in C$_6$H$_4$), 134.93 and 138.18 (2×quaternary C in C$_6$H$_4$), 176.64 and 176.71 (2×C=O); m/z (chemical ionisation, NH$_3$) 474 [(M+H)$^+$, 100%] and 344 [26]; (Found C 68.77, H 6.80, N 2.80; C$_{27}$H$_{31}$NO$_3$Fe requires C 68.51, H 6.60, N 2.96%).

EXAMPLE 7

(2S,4R)-4-Cinnamyl-2-ferrocenyl-4-methyl-3-pivaloyl-1,3-oxazolidin-5-one

Starting with 174.9 mg of the oxazolidinone from Example 2 and following the above general procedure using distilled cinnamyl bromide as electrophile, the title compound was obtained; $\delta_H$ (200 MHz; CDCl$_3$) 1.00 (9H, s, C(CH$_3$)$_3$), 1.97 (3H, s, NCCH$_3$), 2.70 (1H, dd, J 6 Hz, 14 Hz, CH$_A$H$_B$), 3.53 (1H, dd, J 9 Hz, 14 Hz, CH$_A$H$_B$), 4.19–4.34 (4H, m, Cp), 4.28 (5H, s, Cp'), 5.93 (1H, ddd, J 6 Hz, 9 Hz, 15.5 Hz, CH$_2$CH=CHPh), 6.45 (1H, d, J 15.5 Hz, CH$_2$CH=CHPh), 6.64 (1H, s, OCHN), 7.22–7.39 (5H, m, C$_6$H$_5$).

EXAMPLE 8

(2S,4R)-4-(Naphth-2-ylmethyl)-2-ferrocenyl-4-methyl-3-pivaloyl-1,3-oxazolidin-5-one Starting with 126.3 g of the oxazolidinone from Example 2 and following the above general procedure using 2-(bromomethyl)naphthalene as electrophile in solution in tetrahydrofuran (prepared by dissolving the electrophile in dichloromethane, adding tetrahydrofuran and removing the dichloromethane in vacuo), the title compound was obtained as pale orange crystals (166.2 g, 95%) with >98% d.e. (>88% e.e. for the major diastereomer); m.p. 155°–158° C.; [α]$^{23}_D$ –49.6 (c 1.1, CHCl$_3$); ν$_{max}$ (KBr disc) 2979 w (C—H), 1783 s (OC=O), 1647 m (NC=O), 1348 m, 1248 m and 1172 m cm$^{-1}$; $\delta_H$ (200 MHz; CDCl$_3$) 0.79 (9H, s, C(CH$_3$)$_3$), 2.10 (3H, s, NCCH$_3$), 3.36 (1H, d, J 13.5 Hz, CH$_A$H$_B$), 4.02 (1H, d, J 13.5 Hz, CH$_A$H$_B$), 4.22–4.25 and 4.30 (4H, 2 m, Cp,), 4.27 (5H, s, Cp'), 6.02 (1H, s, OCHN), 7.26–7.31, 7.45–7.50, 7.61 and 7.76–7.85 (7H, m, C$_{10}$H$_7$); $\delta_c$ (50.3 MHz; CDCl$_3$) 23.63 (NCCH$_3$), 28.01 (C(CH$_3$)$_3$), 40.85 (C(CH$_3$)$_3$), 41.33 (CH$_2$), 66.50 (NCCH$_3$), 67.96, 68.67, 69.24 and 69.33 (9×CH in Cp and Cp'), 86.82 (OCHN), 89.03 (quaternary C in Cp), 125.93, 126.31, 127.80, 127.90, 128.16 and 129.06 (7×CH in naphthalene), 132.75, 133.48 and 133.80 (3×quaternary C in naphthalene), 176.02 and 176.79 (2×C=O); m/z (chemical ionisation, NH$_3$) 510 [(M+H)$^+$, 100%], 102 [63] and 85 (61); (Found C 70.75, H 6.49, N 2.93; C$_{30}$H$_{31}$NO$_3$Fe requires C 70.73, H 6.13, N 2.75%).

EXAMPLE 9

(2S,4R)-4-(1-t-Butyloxycarbonylindol-3-ylmethyl)-2-ferrocenyl-4-methyl-3-pivaloyl-1,3-oxazolidin-5-one Starting with 1.310 g of the oxazolidinone from Example 2 and following the general procedure using 1-(t-butyloxycarbonyl)-3-(bromomethyl)indole [U. Schoellkopf, R. Lonsky, P. Lehr Liebigs Ann. Chem. 1985, 413] in solution in tetrahydrofuran as electrophile, the title compound was obtained (1.741 g, 82%); $\delta_H$ (200 MHz; CDCl$_3$) 0.83 (9H, s, COC(CH$_3$)$_3$), 1.67 (9H, s, CO$_2$C(CH$_3$)$_3$), 2.10 (3H, s, NCCH$_3$), 3.31 (1H, d, J 14.5 Hz, CH$_A$H$_B$), 4.02 (1H, d, J 14.5 Hz, CH$_A$H$_B$), 4.16–4.27 (4H, m, Cp), 4.25 (5H, s, Cp'), 6.20 (1H s, OCHN), 7.25–7.37, 7.62–7.70 and 8.15–8.18 (5H, 3 m, C$_8$H$_5$N).

EXAMPLE 10

(2S,4R)-4-Cyanomethyl-2-ferrocenyl-4-methyl-3-pivaloyl-1,3-oxazolidin-5-one

Starting with 224.1mg of the oxazolidinone from Example 2 and following the above general procedure using bromoacetonitrile as electrophile, the title compound was obtained; $\delta_H$ (200 MHz; CDCl$_3$), 1.12 (9H, s, C(CH$_3$)$_3$), 1.93 (3H, NCCH$_3$), 2.89 (1H, d, J 16.5 Hz, CH$_A$H$_B$), 3.83 (1H, d, J 16.5 Hz, CH$_A$H$_B$), 4.18–4.29 (4H, m, Cp), 4.28 (5H, s, Cp') and 6.88 (1H, s, OCHN).

General Hydrolysis Procedure to Form Free Amino Acid

A glass column was filled with distilled water and Amberlyst-15 was added slowly and in several portions into the column. It was washed with distilled water up to pH 3 and then with acetone-distilled water (9:1). The substituted oxazolidinone was dissolved in acetone-distilled water (9:1); a gentle warming was sometimes needed to complete dissolution. The resulting solution was poured into the column and left overnight. Elution with acetone-distilled water (9:1), removal of the acetone in vacuo, followed by extraction of the aqueous solution with diethyl ether and purification by column chromatography (silicagel-petroleum ether; 90:20) yielded ferrocenecarboxaldehyde. The column was then eluted with 2% ammonium hydroxide. The aqueous solution was concentrated in vacuo to yield free amino acid.

EXAMPLE 11

(R)-(+)-α-Methylphenylalanine

Starting with 3.0 g of (2S,4R)-4-benzyl-2-ferrocenyl-4-methyl-3-pivaloyl-1,3-oxazolidin-5-one from Example 3 and following the above general hydrolysis procedure, ferrocenecarboxaldehyde (0.89 g, 76%) and free amino acid were obtained. The latter was dissolved in methanol and passed through a sinter containing decolourising charcoal to yield, after removing the solvent, the title compound (0.89 g, 76%) as colourless crystals; $[\alpha]_{578}^{25}+17$ (c 0.1, MeOH) [F. W. Bollinger *J. Med. Chem.* 1971, 14, 373 and D. Seebach, A. Fadel *Helv. Chim. Acta* 1985, 68, 1243 give m.p. 307°–308° C. dec. and $[\alpha]_{578}^{24}+20$ (c 0.1 MeOH)]. This product proved difficult to dehydrate, showed a tendency to rehydrate, and was easily oxidisable by air. The corresponding hydrochloride was prepared as described by Bollinger (op. cit.); $v_{max}$ (KBr disc) 3436 (N—H), 3034 (HC=C), 1619 ($CO_2^-$) and 1583 (C=C) $cm^{-1}$; $\delta_H$ (200 MHz; $CH_3OD$) 1.50 (3H, s, $CH_3$), 2.92 (1H, d, J 14 Hz, C $H_AH_B$), 3.28 (1H, d, J 14 Hz, $CH_AH_B$) and 7.29 (5H, m, $C_6H_5$); $\delta_c$ (50.3 MHz, $CH_3OD$) 21.5 ($CH_3$), 42.6 ($CH_2$), 60.7 ($CCH_3$), 127.6, 128.7, 130.2, 134.1 (5×$CCH$ in $C_6H_5$) and 173.9 (C=O); m/z 180 [(M+H)$^+$, 100%], 134[16] and 88[21]; (Found: C, 55.86; H, 6.77; N, 6.72; $C_{10}H_{14}NO_2Cl$ requires C, 55.69; H, 6.54; N, 6.49%)

EXAMPLE 12

(R)-(+)-α-Methylallylalanine

Starting with 1.843 g of (2S,4R)-4-allyl-2-ferrocenyl-4-methyl-3-pivaloyl-1,3-oxazolidin-5-one from Example 4 and following the above general hydrolysis procedure, ferrocenecarboxaldehyde (0.815 g, 85%) and free amino acid were obtained. The latter was dissolved in methanol and passed through a sinter containing decolourising charcoal to yield, after removing the solvent, the title compound as colourless crystals (0.555 g, 95%); m.p. 296°–299° C.; $[\alpha]^{25}_D+24.1$ (c 0.7, MeOH); $[\alpha]^{22}_D+6.1$ (c 1.3, $D_2O$); $v_{max}$ (KBr disc) 3021 s br (OCO—H), 1645 s (C=O), 1575 s and 1545 s $cm^{-1}$; $\delta_H$ (200 MHz; $D_2O$) 1.47 (3H, s, $CH_3$), 2.43 (1H, dd, J 8 Hz, 14.5 Hz, $CH_AH_B$), 2.65 (1H, dd, J 6.5 Hz, 14.5 Hz, $CH_AH_B$), 5.22 (1H, d, J 4 Hz, CH=$CH_2$), 5.28 (1H, s, CH=$CH_2$) and 5.63–5.84 (1H, m, $CH$=$CH_2$); $\delta_c$ (50.3 MHz, $CH_3OD$) 21.40 ($CH_3$), 41.49 ($CH_2CH$=$CH_2$), 59.96 ($CCH_3$), 120.05 ($CH_2CH$=$C_2$) and 131.20 ($CH_2$ $CH$=$CH_2$); m/z (desorption chemical ionisation, $NH_3$) 130 [(M+H)$^+$, 100%], 88 [21] and 84 [17].

EXAMPLE 13

(R)-(+)-α-methyl-(2-methylbenzyl)alanine

Starting with (2S,4R)-4-(2-methylbenzyl)-2-ferrocenyl-4-methyl-3-pivaloyl-1,3-oxazolidin-5-one from Example 6 and following the above general hydrolysis procedure, fer-rocenecarboxaldehyde and the title compound were obtained; $\delta_H$ (200 MHz; $D_2O$) 1.30 and 2.09 (2×3H, 2×s, C $H_3$), 2.91 (1H, d, J 14.5 Hz, $CH_AH_B$), 3.02 (1H, d, J 14.5 Hz, $CH_AH_B$) and 6.96–7.04 (4H, m, $C_6H_4$).

We claim:
1. Chiral compounds of formula (V)

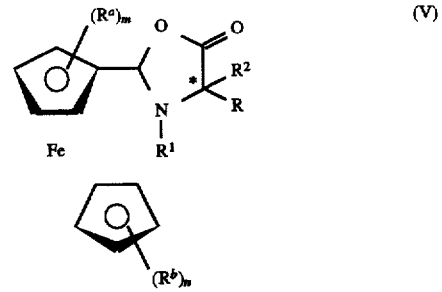

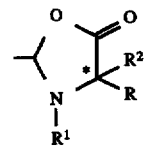

where R represents a hydrogen atom or an organic group selected from the group consisting of optionally substituted aliphatic, cycloaliphatic and araliphatic groups containing up to 20 carbon atoms; $R^1$ represents an N-protecting group; $R^2$ represents an organic group selected from the group consisting of optionally substituted aliphatic and araliphatic groups containing up to 20 carbon atoms; $R^a$ and $R^b$, which may be the same or different, are each selected from the group consisting of lower alkyl, lower alkoxy, lower alkylthio, lower alkylsulphonyl, lower alkanoyl, lower alkanoyloxy, lower alkoxycarbonyl, disubstituted amino, disubstituted aminoalkyl, lower alkanoylamino, $C_{6-12}$ aryl-$C_{1-4}$ alkyl, $C_{6-20}$ aryl, carbamoyl, sulphamoyl, nitro and halo, or $R^b$ is an oxazolidinone group of formula:

$$-\underset{\underset{R^1}{|}}{\underset{N}{\overset{\overset{O}{|}}{C}}}\overset{*}{C}\overset{O}{\underset{R}{\overset{||}{C}}}R^2$$

m is 0 or an integer of 1–4; n is 0 or an integer of 1–5; and the asterisk denotes that the configuration of R and $R^2$ is such that the compound is in substantially enantiomerically pure form.

2. Compounds as claimed in claim 1 wherein R is selected from the group consisting of hydrogen, methyl, isopropyl, isobutyl, sec-butyl, optionally protected hydroxymethyl, optionally protected 1-hydroxyethyl, optionally protected mercaptomethyl, optionally protected carboxymethyl, optionally protected 2-carboxyethyl, carbamoylmethyl, 2-carbamoylethyl, 2-(methylthio)ethyl, optionally protected 4-aminobutyl, benzyl, optionally protected p-hydroxybenzyl, optionally protected indol-3-ylmethyl, optionally protected imidazol-4-ylmethyl, and optionally protected 3-guanidinopropyl.

3. Compounds as claimed in claim 1 wherein $R^1$ is a lower alkanoyl, lower alkoxycarbonyl, lower alkylsuphonyl, aryl sulphonyl, tri(lower alkyl)silyl, camphanyl or camphasulphonyl group.

4. Compounds as claimed in claim 1 wherein $R^2$ is an optionally substituted lower alkyl, lower alkenyl, carbocyclic or heterocyclic aryl lower alkyl or carbocyclic or heterocyclic aryl lower alkenyl group.

5. Compounds as claimed in claim 4 wherein $R^2$ represents a cyanomethyl, allyl, crotyl, benzyl, 2-methylbenzyl, naphth-2-ylmethyl, N-protected indol-3-ylmethyl or cinnamyl group.

6. Compounds as claimed in claim 2 wherein m and n are both 0.

7. Compounds as claimed in claim 1 wherein m is 1 and the substituent $R^a$ is positioned ortho to the 1,3-oxazolidin-5-one ring.

8. Compounds as claimed in claim 1 wherein n is at least 1 and at least one $R^b$ substituent is a group of formula

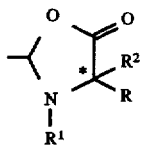

where R, $R^1$, $R^2$ and the meaning of the asterisk are as defined in claim 1.

9. The compounds:

(2S,4R)-4-benzyl-2-ferrocenyl-4-methyl-3-pivaloyl-1,3-oxazolidin-5-one;

(2S,4R)-4-allyl-2-ferrocenyl-4-methyl-3-pivaloyl-1,3-oxazolidin-5-one;

(2S,4R)-4-crotyl-2-ferrocenyl-4-methyl-3-pivaloyl-1,3-oxazolidin-5-one;

(2S,4R)-4-(2-methylbenzyl)-2-ferrocenyl-4-methyl-3-pivaloyl-1,3-oxazolidin-5-one;

(2S,4R)-4-cinnamyl-2-ferrocenyl-4-methyl-3-pivaloyl-1,3-oxazolidin-5-one;

(2S,4R)-4-(naphth-2-ylmethyl)-2-ferrocenyl-4-methyl-3-pivaloyl-1,3-oxazolidin-5-one;

(2S,4R)-4-(1-t-butoxycarbonylindol-3-ylmethyl)-2-ferrocenyl-4-methyl-3-pivaloyl-1,3-oxazolidin-5-one; and (2S,4R)-4-cyanomethyl-2-ferrocenyl-4-methyl-3-pivaloyl-1,3-oxazolidin-5-one.

10. Chiral compounds of formula (IV)

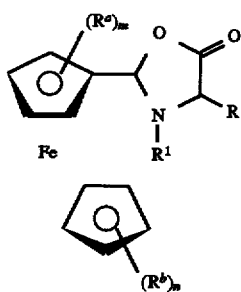

(IV)

where R represents a hydrogen atom or an organic group selected from the group consisting of optionally substituted aliphatic, cycloaliphatic and araliphatic groups containing up to 20 carbon atoms; $R^1$ represents an N-protecting group: $R^a$ and $R^b$, which may be the same or different, are each selected from the group consisting of lower alkyl, lower alkoxy, lower alkylthio, lower alkylsulphonyl, lower alkanoyl, lower alkanoyloxy, lower alkoxycarbonyl, disubstituted amino, disubstituted aminoalkyl, lower alkanoylamino. $C_{6-12}$ aryl-$C_{1-4}$ alkyl, $C_{6-20}$ aryl, carbamoyl, sulphamoyl, nitro and halo, or at least one of $R^b$ is an oxazolidinone group of formula:

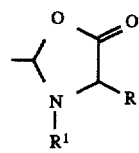

m is 0 or an integer of 1–4; and n is 0 or an integer of 1–5.

11. Compounds as claimed in claim 10 wherein R is selected from the group consisting of hydrogen, methyl, isopropyl, isobutyl, sec-butyl, optionally substituted hydroxymethyl, optionally substituted 1-hydroxyethyl, optionally substituted mercaptomethyl, optionally substituted carboxymethyl, optionally substituted 2-carboxyethyl, carbamoylmethyl, 2-carbamoylethyl, 2-(methylthio)ethyl, optionally substituted 4-aminobutyl, benzyl, optionally substituted p-hydroxybenzyl, optionally substituted indol-3-ylmethyl, optionally substituted imidazol-4-ylmethyl, and optionally substituted 3-guanidinopropyl.

12. Compounds as claimed in claim 10 wherein $R^1$ is a lower alkanoyl, lower alkoxycarbonyl, lower alkylsulphonyl, aryl sulphonyl, tri(lower alkyl)silyl, camphanyl or camphasulphonyl group.

13. Compounds as claimed in any of claim 10 wherein m and n are both 0.

14. Compounds as claimed in claim 10 wherein m is 1 and the substituent $R^a$ is positioned ortho to the 1,3-oxazolidin-5-one ring.

15. Compounds as claimed in claim 10 wherein n is at least 1 and at least one $R^b$ substituent is a group of formula

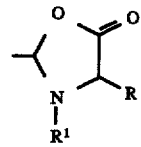

where R and $R^1$ are as defined in claim 1.

16. (2S,4S)-4-Ferrocenyl-4-methyl-3-pivaloyl-1,3-oxazolidin-5-one.

17. A process for the preparation of a chiral compound of formula (IV) as claimed in claim 10 wherein an α-amino acid or salt of formula (I)

(I)

wherein R is as defined in claim 10 and X represents a hydrogen atom or a cation is reacted with a compound of formula (II)

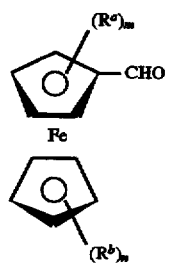

(II)

wherein $R^a$, $R^b$, m and n are as defined in claim 10 to yield a Schiff's base of formula (III)

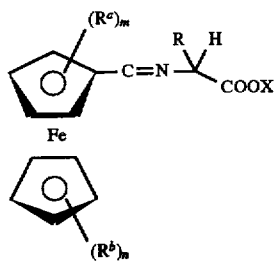 (III)

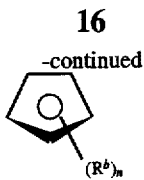 (-continued)

wherein R, $R^a$, $R^b$, m and n are as defined in claim 10 and X is as defined in this claim and said compound (III) is reacted with a compound serving to introduce an N-protecting group at the imine nitrogen atom to yield said compound of formula (IV).

18. Ferrocene carboxaldehyde sodium L-alaninate imine.

19. A process for the preparation of a compound of formula (V) as claimed in claim 2 wherein a compound of formula (IV)

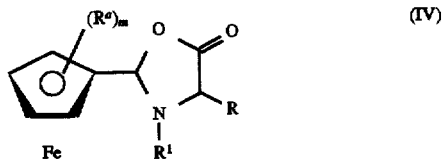 (IV)

where R represents a hydrogen atom or an organic group selected from the group consisting of optionally substituted aliphatic, cycloaliphatic and araliphatic groups containing up to 20 carbon atoms; $R^1$ represents an N-protecting group; $R^a$ and $R^b$, which may be the same or different, are each selected from the group consisting of lower alkyl, lower alkoxy, lower alkylthio, lower alkylsulphonyl, lower alkanoyl, lower alkanoyloxy, lower alkoxycarbonyl, disubstituted amino, disubstituted aminoalkyl, lower alkanoylamino, $C_{6-12}$ aryl-$C_{1-4}$ alkyl, $C_{6-20}$ aryl, carbamoyl, sulphamoyl, nitro and halo, or $R^b$ is an oxazolidinone group of formula;

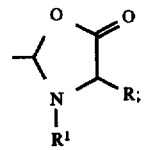

m is 0 or an integer of 1–4; and n is 0 or an integer of 1–5, is subjected to electrophilic substitution to yield said compound of formula (V).

* * * * *